United States Patent [19]

Andree et al.

[11] Patent Number: 5,108,489
[45] Date of Patent: Apr. 28, 1992

[54] HERBICIDAL DISUBSTITUTED NAPHTHALENES

[75] Inventors: Roland Andree, Langenfeld; Michael Haug, Bergisch Gladbach; Hans-Joachim Santel, Leverkusen; Robert R. Schmidt, Bergisch Gladbach; Harry Strang, Duesseldorf, all of Fed. Rep. of Germany

[73] Assignee: Bayer Aktiengesellschaft, Leverkusen, Fed. Rep. of Germany

[21] Appl. No.: 734,101

[22] Filed: Jul. 24, 1991

Related U.S. Application Data

[63] Continuation of Ser. No. 400,305, Aug. 29, 1989, abandoned.

[30] Foreign Application Priority Data

Sep. 1, 1988 [DE] Fed. Rep. of Germany ....... 3829586

[51] Int. Cl.$^5$ .......................................... A01N 37/12
[52] U.S. Cl. ........................ 71/111; 71/105; 71/103; 71/98; 71/123; 71/121; 71/118; 568/328; 568/42; 560/32; 560/10; 564/162; 564/174; 564/257; 564/265; 558/414; 558/418
[58] Field of Search .............. 71/103, 105, 98, 111, 71/118, 123, 121; 568/328, 42; 560/38, 10; 564/162, 174, 257, 265; 558/414, 418

[56] References Cited

U.S. PATENT DOCUMENTS

| 4,548,756 | 10/1985 | Martin | 560/35 |
| 4,709,077 | 11/1987 | Harre et al. | 71/114 |

FOREIGN PATENT DOCUMENTS

| 0023891 | 2/1981 | European Pat. Off. | 71/98 |
| 0200686 | 11/1986 | European Pat. Off. | 71/98 |
| 2223894 | 5/1972 | Fed. Rep. of Germany | 71/104 |
| 3220425 | 12/1983 | Fed. Rep. of Germany | 71/98 |
| 670084 | 5/1989 | Switzerland | 71/98 |
| 1096037 | 1/1966 | United Kingdom | 564/257 |

*Primary Examiner*—James H. Reamer
*Attorney, Agent, or Firm*—Sprung, Horn, Kramer & Woods

[57] ABSTRACT

Herbicidal disubstituted naphthalenes of the formula

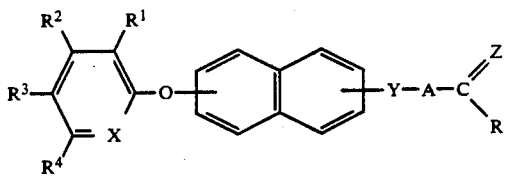

in which
A represents optionally branched alkanediyl,
R represents hydrogen or in each case optionally substituted alkyl or phenyl,
$R^1$ represents hydrogen, halogen, cyano or trifluoromethyl,
$R^2$ represents hydrogen or halogen,
$R^3$ represents halogen, trifluoromethyl, trifluoromethoxy, trifluoromethylthio or trifluoromethylsulphonyl,
$R^4$ represents hydrogen or halogen,
X represents nitrogen or the group C—$R^5$, where $R^5$ represents hydrogen or halogen,
Y represents oxygen or sulphur, and
Z represents oxygen, the group N—(O)$_n$—$R^6$ or

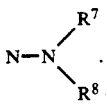

7 Claims, No Drawings

HERBICIDAL DISUBSTITUTED NAPHTHALENES

This application is a continuation of application Ser. No. 400,305, filed Aug. 29, 1989, now abandoned.

The invention relates to novel disubstituted naphthalenes, processes for their preparation, and their use as herbicides.

It has already been disclosed that certain dioxy-benzene derivatives, such as, for example, methyl α-[4-(2,4-dichloro-phenoxy)-phenoxy]-propionate (diclofop-methyl), are herbicidally active (cf. DE-OS (German Published Specification) 2,223,894). However, the action of these known compounds against weeds, as well as their tolerance by crop plants, are not always satisfactory.

Novel disubstituted naphthalenes of the general formula (I)

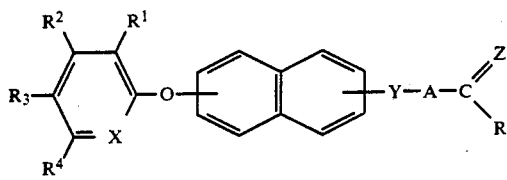

in which
A represents optionally branched alkanediyl,
R represents hydrogen or in each case optionally substituted alkyl or phenyl,
$R^1$ represents hydrogen, halogen, cyano or trifluoromethyl,
$R^2$ represents hydrogen or halogen,
$R^3$ represents halogen, trifluoromethyl, trifluoromethoxy, trifluoromethylthio or trifluoromethylsulphonyl,
$R^4$ represents hydrogen or halogen,
X represents nitrogen or the group C—$R^5$, where $R^5$ represents hydrogen or halogen,
Y represents oxygen or sulphur, and
Z represents oxygen, the group N—(O)$_n$—$R^6$ or

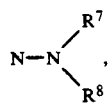

where
n represents the numbers 0 or 1 and
$R^6$ represents hydrogen or an optionally substituted radical from the series comprising alkyl, alkenyl, alkinyl, cycloalkyl, cycloalkylalkyl, aralkyl and aryl,
$R^7$ represents hydrogen or alkyl and
$R^8$ represents hydrogen or an optionally substituted radical from the series comprising alkyl, alkenyl, alkinyl, cycloalkyl, aralkyl, aryl, alkylcarbonyl, alkoxycarbonyl, alkylsulphonyl, arylsulphonyl and heteroaryl,
have now been found.

Furthermore, it has been found that the novel disubstituted naphthalenes of the general formula (I) are obtained when (a) substituted hydroxy- or mercaptonaphthalenes of the general formula (II)

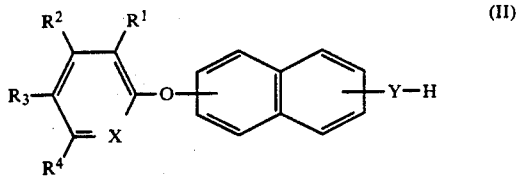

in which $R^1$, $R^2$, $R^3$, $R^4$, X and Y have the abovementioned meanings, are reacted with alkylating agents of the general formula (III)

in which A, R and Z have the abovementioned meanings and $X^1$ represents halogen, —in the event that Z represents oxygen, if appropriate with corresponding dimethyl or diethyl acetals or ketals—if appropriate in the presence of an acid acceptor and if appropriate in the presence of a diluent, or when (b) in the event that Z represents the group N—(O)$_n$—$R^6$ or the group

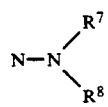

corresponding carbonyl compounds of the formula (Ia)

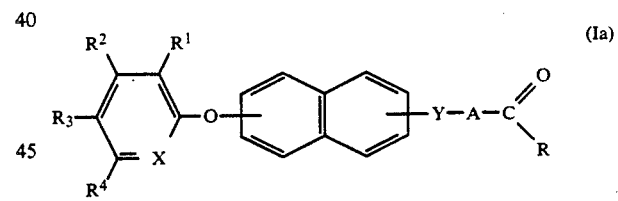

in which A, R, $R^1$, $R^2$, $R^3$, $R^4$, X and Y have the abovementioned meanings, are reacted with amino compounds of the formulae (IV) or (V)

where n, $R^6$, $R^7$ and $R^8$ have the abovementioned meanings, or with the hydrochlorides thereof, if appropriate in the presence of a catalyst and if appropriate in the presence of a diluent, or when (c) in the event that Z represents the group N—O—$R^6$, corresponding hydroximino compounds of the formula (Ib)

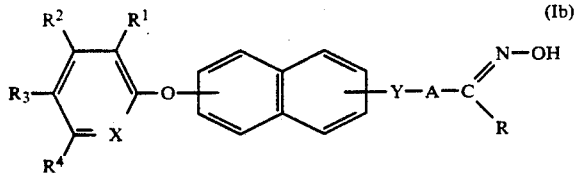

in which A, R, $R^1$, $R^2$, $R^3$, $R^4$, X and Y have the abovementioned meanings, are reacted with alkylating agents of the formula (VI)

$$X^2-R^6 \quad (VI)$$

in which $R^6$ has the abovementioned meaning and $X^2$ represents halogen, alkylsulphonyloxy or arylsulphonyloxy, if appropriate in the presence of a diluent.

Finally, it has been found that the novel disubstituted naphthalenes of the general formula (I) possess herbicidal properties.

Surprisingly, the disubstituted naphthalenes of the formula (I) according to the invention show a considerably better action against problem weeds than methyl α-(4-(2,4-dichloro-phenoxy)-phenoxy)-propionate, which is a structurally similar, previously known active compound of the same direction of action, while being well tolerated by crop plants.

The carbon chains in the individual radicals, such as, for example, alkyl, alkenyl, alkinyl, cycloalkyl, cycloalkylalkyl, alkylcarbonyl, alkoxycarbonyl or alkylsulphonyl, are in each case straight-chain or branched.

The invention preferably relates to compounds of the formula (I) in which

A represents optionally branched $C_1$-$C_4$-alkanediyl,

R represents hydrogen, $C_1$-$C_6$-alkyl or phenyl, $R^1$ represents hydrogen, fluorine, chlorine, bromine, cyano or trifluoromethyl, $R^2$ represents hydrogen, fluorine or chlorine, $R^3$ represents fluorine, chlorine, bromine, trifluoromethyl, trifluoromethoxy, trifluoromethylthio or trifluoromethylsulphonyl, $R^4$ represents hydrogen, fluorine or chlorine, X represents nitrogen or the group C—$R^5$ where $R^5$ represents hydrogen, fluorine, chlorine or bromine, Y represents oxygen or sulphur, and Z represents oxygen, the group N—(O)$_n$—$R^6$ or

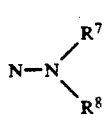

where n represents the numbers 0 or 1 and $R^6$ represents hydrogen, halogeno-$C_1$-$C_8$-alkyl, where halogen in particular represents fluorine or chlorine, or $R^6$ represents $C_1$-$C_8$-alkyl which is optionally substituted by $C_1$-$C_4$-alkoxy, $C_1$-$C_4$-alkylthio, $C_1$-$C_4$-alkylsulphinyl, $C_1$-$C_4$-alkylsulphonyl, carboxyl, $C_1$-$C_4$-alkoxy-carbonyl, $C_1$-$C_4$-alkylamino-carbonyl, di-($C_1$-$C_4$-alkyl)-amino-carbonyl, N-($C_1$-$C_4$-alkyl)-phenylamino-carbonyl or cyano, or represents $C_2$-$C_6$-alkenyl, halogeno-$C_2$-$C_6$-alkenyl, $C_3$-$C_6$-alkinyl, $C_3$-$C_6$-cycloalkyl, $C_3$-$C_6$-cycloalkyl-$C_1$-$C_2$-alkyl, or represents benzyl, phenylethyl, benzhydryl or phenyl, which are in each case optionally substituted in the aromatic moiety by fluorine, chlorine, bromine, cyano, nitro, $C_1$-$C_4$-alkyl, $C_1$-$C_4$-alkoxy and/or $C_1$-$C_4$-alkoxy-carbonyl, $R^7$ represents hydrogen or $C_1$-$C_4$-alkyl and $R^8$ presents hydrogen, halogeno-$C_1$-$C_4$-alkyl, where halogen in particular represents fluorine or chlorine, or $R^8$ represents $C_1$-$C_4$-alkyl which is optionally substituted by cyano, nitro, $C_1$-$C_4$-alkoxy or $C_1$-$C_4$-alkoxy-carbonyl, $R^8$ further represents $C_3$-$C_6$-alkenyl, $C_3$-$C_6$-alkinyl, $C_3$-$C_6$-cycloalkyl, or represents benzyl, phenylethyl, benzylhydryl or phenyl, which are in each case optionally substituted in the aromatic moiety by fluorine, chlorine, bromine, cyano, nitro, $C_1$-$C_4$-alkyl, trifluoromethyl, $C_1$-$C_4$-alkoxy, difluoromethoxy, trifluoromethoxy, $C_1$-$C_4$-alkylthio, trifluoromethylthio or $C_1$-$C_4$-alkoxy-carbonyl, or represents $C_1$-$C_4$-alkylcarbonyl, $C_1$-$C_4$-alkoxy-carbonyl, $C_1$-$C_4$-alkylsulphonyl, phenylsulphonyl or naphthylsulphonyl, where phenylsulphonyl or naphthylsulphonyl are optionally substituted by fluorine, chlorine, bromine, cyano, nitro, $C_1$-$C_4$-alkyl, trifluoromethyl, $C_1$-$C_4$-alkoxy, difluoromethoxy, trifluoromethoxy, $C_1$-$C_4$-alkylthio, trifluoromethylthio and/or $C_1$-$C_4$-alkoxy-carbonyl, or $R^8$ represents pyrimidinyl.

In particular, the invention relates to compounds of the formula (I) in which

A represents methylene (—$CH_2$—), dimethylene (—$CH_2CH_2$—), trimethylene (—$CH_2CH_2CH_2$—), ethylidene

or propylidene

R represents methyl, ethyl, propyl, isopropyl, butyl, isobutyl, sec-butyl or tert-butyl, $R^1$ represents cyano, fluorine or chlorine, $R^2$ represents hydrogen, fluorine or chlorine, $R^3$ represents chlorine, trifluoromethyl or trifluoromethylsulphonyl, $R^4$ represents hydrogen, fluorine or chlorine, X represents nitrogen or the group C—$R^5$, where $R^5$ represents hydrogen, fluorine or chlorine, Y represents oxygen or sulphur, and Z represents oxygen, the group N—(O)$_n$—$R^6$ or

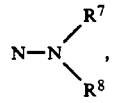

where n represents the numbers 0 or 1 and $R^6$ represents hydrogen, $C_1$-$C_4$-alkyl, $C_3$-$C_4$-alkenyl, $C_1$-$C_3$-alkoxy-carbonyl-$C_1$-$C_2$-alkyl, $C_1$-$C_3$-alkylaminocarbonyl-$C_1$-$C_2$-alkyl, di-($C_1$-$C_3$-alkyl)- amino-carbonyl-$C_1$-$C_2$-alkyl, N-($C_1$-$C_3$-alkyl)-phenylaminocarbonyl-$C_1$-$C_2$-alkyl, or benzyl which is optionally substituted in the aromatic moiety by fluorine, chlorine, methyl, methoxy and/or methoxycarbonyl, $R^7$ represents hydrogen or methyl and $R^8$ represents $C_1$-$C_4$-alkyl, phenyl which is optionally substituted by fluorine, chlorine, bromine, methyl, ethyl, trifluoromethyl, methoxy, ethoxy, difluoromethoxy and/or trifluoromethoxy, or represents acetyl, propionyl, methoxycarbonyl, ethoxycarbonyl, methylsulphonyl, ethylsulphonyl, phenylsulphonyl or tolylsulphonyl.

Very particularly preferred groups of compounds of the formula (I) are those of the formulae (IA) to (IE) below, in which A, R, $R^1$, $R^2$, $R^3$, $R^4$, X, Y and Z in each case have the meanings which are mentioned above as particularly preferred.

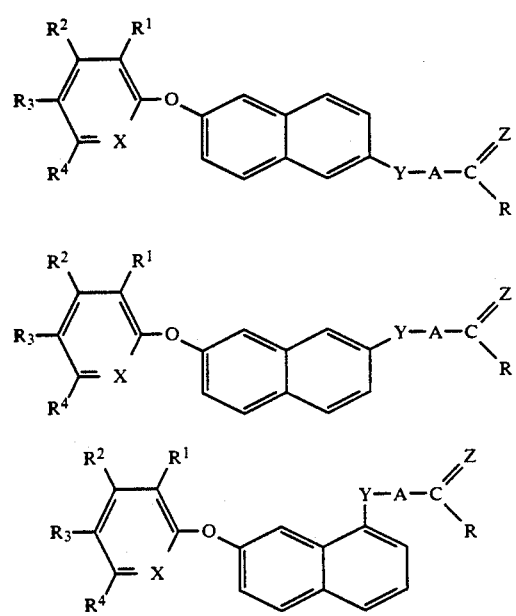

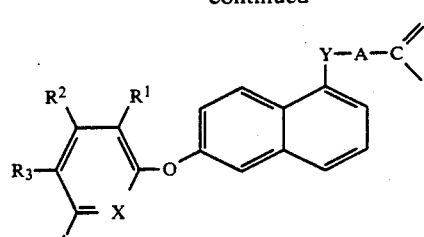

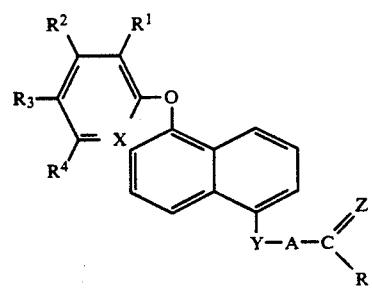

If 7-(3-chloro-5-trifluoromethyl-pyridin-2-yl-oxy)-naphthalen-1-yl-mercaptan and chloromethyl tert-butyl ketone are used as starting substances in process (a) according to the invention, the course of the reaction can be represented by the following equation:

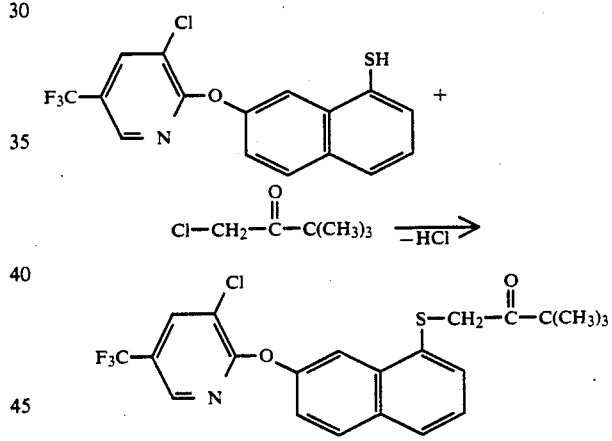

If 7-(2,6-dichloro-4-trifluoromethyl-phenoxy)-naphthalen-2-yl-oxy-methyl) methyl ketone and methanesulphonic acid hydrazide are used as starting substances in process (b) according to the invention, the course of the reaction can be represented by the following equation:

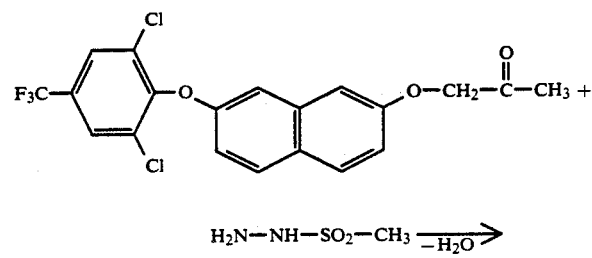

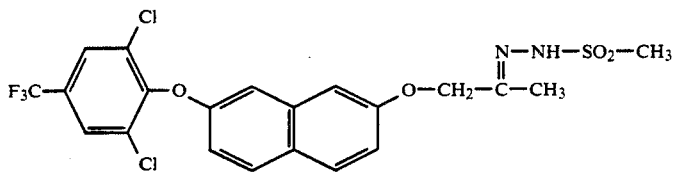

If 5-(3,5-dichloro-pyridin-2-yl-oxy)-1-(3-hydroximinobutan-2-yl-oxy)-naphthalene and butyl bromoacetate are used as starting substances in process (c) according to the invention, the course of the reaction can be represented by the following equation:

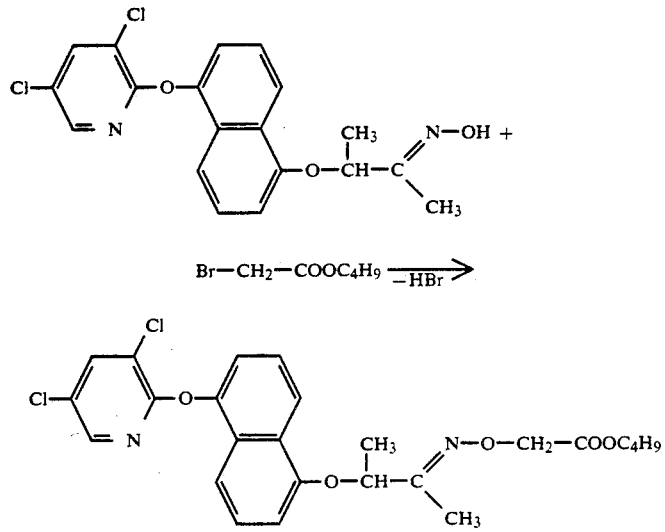

Formula (II) provides a general definition of the hydroxy- or mercaptonaphthalenes to be used as starting substances in process (a) according to the invention for the preparation of compounds of the formula (I).

In formula (II), $R^1$, $R^2$, $R^3$, $R^4$, X and Y preferably, or in particular, have those meanings which have already been mentioned above in connection with the description of the compounds of the formula (I) according to the invention as being preferred, or particularly preferred, for $R^1$, $R^2$, $R^3$, $R^4$, X and Y.

Examples of the starting substances of the formula (II) ar listed in Table 1 below.

The individual examples listed in Table 1 hold for very particularly preferred groups of compounds of the formula (I), which are outlined above by the formulae (IA), (IB), (IC), (ID) and (IE).

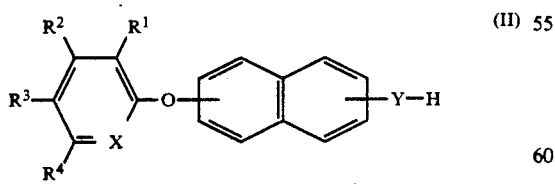

TABLE 1

| Examples of the starting substances of the formula (II) | | | | | |
|---|---|---|---|---|---|
| $R^1$ | $R^2$ | $R^3$ | $R^4$ | X | Y |
| Cl | H | Cl | H | CH | O |
| Cl | H | Cl | H | CH | S |
| Cl | H | Cl | H | N | O |

TABLE 1-continued

| Examples of the starting substances of the formula (II) | | | | | |
|---|---|---|---|---|---|
| $R^1$ | $R^2$ | $R^3$ | $R^4$ | X | Y |
| Cl | H | Cl | H | N | S |
| Cl | H | CF$_3$ | H | CH | O |
| Cl | H | CF$_3$ | H | CH | S |
| Cl | H | CF$_3$ | H | N | O |
| Cl | H | CF$_3$ | H | N | S |
| Cl | H | CF$_3$ | H | C—Cl | O |
| Cl | H | CF$_3$ | H | C—Cl | S |
| Cl | H | CF$_3$ | H | C—F | O |
| Cl | H | CF$_3$ | H | C—F | S |
| Cl | H | CF$_3$ | F | C—Cl | O |
| Cl | H | CF$_3$ | F | C—Cl | S |
| Cl | H | CF$_3$ | Cl | C—Cl | O |
| Cl | H | CF$_3$ | Cl | C—Cl | S |
| CN | H | CF$_3$ | H | CH | O |
| Cl | H | SO$_2$CF$_3$ | H | CH | O |
| Cl | H | SO$_3$CF$_3$ | H | C—Cl | O |
| F | H | CF$_3$ | H | C—F | O |

The starting substances of the formula (II) are known or are the subject of patent applications such as EP-A 179,015, DE-A 3,731,801, DE-A 3,733,067, DE-P 3,737,179 of Nov. 3, 1987 and DE-P 3,823,318 of Jul. 9, 1988.

The compounds of the formula (II) are obtained when (α) in the event that Y represents oxygen, halogeno(-hetero)aryl compounds of the general formula (VII)

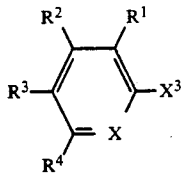

in which

R$^1$, R$^2$, R$^3$, R$^4$ and X have the abovementioned meanings and

X$^3$ represents fluorine or chlorine, are reacted with dihydroxynaphthalenes of the general formula (VIII)

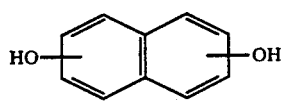

in the presence of an acid acceptor, such as, for example, sodium hydroxide or potassium hydroxide, and in the presence of a diluent, such as, for example, dimethylformamide, dimethylacetamide, dimethyl sulphoxide, tetramethylene sulphone or N-methylpyrrolidone, at temperatures between 20° C. and 150° C., and working up is carried out by customary methods, or (β) in the event that Y represents sulphur, (hetero)aryloxynaphthalenesulphonyl chlorides of the general formula (IX)

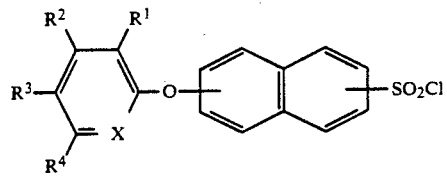

in which R$^1$, R$^2$, R$^3$, R$^4$ and X have the abovementioned meanings, are reacted with reducing agents, such as, for example, zinc dust, if appropriate in the presence of organic solvents, such as, for example, tetrahydrofuran or dioxane, and, if appropriate, in the presence of aqueous mineral acids, such as, for example, hydrochloric acid or sulphuric acid, at temperatures between 0° C. and 150° C., and working up is carried out by customary methods.

Formula (VII) provides a general definition of the halogeno(hetero)aryl compounds required as starting substances. In formula (VII), R$^1$, R$^2$, R$^3$, R$^4$ and X preferably, or in particular, have those meanings which have already been mentioned in connection with the description of the compounds of the formula (I) according to the invention as being preferred, or particularly preferred, for R$^1$, R$^2$, R$^3$, R$^4$ and X.

Examples of the halogeno-(hetero)aryl compounds of the formula (VII) which may be mentioned are: 4-chloro-benzotrifluoride, 3,4-dichloro-benzotrifluoride, 3,4,5-trichloro-benzotrifluoride, 3,4-dichloro-5-fluorobenzotrifluoride, 2,3,4,5-tetrachloro-benzotrifluoride, 3,5-dichloro-2,4-difluoro-benzotrifluoride, 3-chloro-4,5-difluoro-benzotrifluoride, and also 2,3,5-trichloropyridine and 2,3-dichloro-5-trifluoromethyl-pyridine.

The compounds of the formula (VII) are known and/or can be prepared by processes which are known per se (cf. J. Chem. Soc. 1969, 211-217; loc. cit. 1971, 1547-1549; EP-A 34,402; U.S. Pat. No. 4,424,396; EP-A 145,314; FR-A 2,538,380 (Chem. Abstracts 102 (1985), 61914x)).

Examples which may be mentioned of the dihydroxynaphthalenes of the formula (VIII), which are furthermore required as starting substances, are: 1,5-dihydroxy-naphthalene, 1,6-dihydroxy-naphthalene, 1,7-dihydroxy-naphthalene, 2,6-dihydroxy-napthalane and 2,7-dihydroxy-naphthalene.

The compounds of the formula (VIII) are known chemicals for organic synthesis.

Formula (IX) provides a general definition of the (hetero)aryloxynaphthalenesulphonyl chlorides, which are furthermore required as starting substances.

In formula (IX), R$^1$, R$^2$, R$^3$, R$^4$ and X preferably, or in particular, have those meanings which have already been mentioned above in connection with the description of the compounds of the formula (I) according to the invention as being preferred, or particularly preferred, for R$^1$, R$^2$, R$^3$, R$^4$ and X.

Examples which may be mentioned of the starting substances of the formula (IX) are: 5-, 6- and 7-(3,5-dichloro-pyridin-2-yl-oxy)-, -(2-chloro-4-trifluoromethyl-phenoxy)-, -(2,6-dichloro-4-trifluoromethyl-phenoxy)-, -(2-chloro-6-fluoro-4-trifluoromethyl-phenoxy)-, -(2,3,6-trichloro-4-trifluoromethyl-phenoxy)- and (2,6-dichloro-3-fluoro-4-trifluoromethyl-phenoxy)-naphthalene-1-sulphonyl chloride, and also 6- and 7-(3,5-dichloro-pyridin-2-yl-oxy)-, -(2-chloro-4-trifluoromethyl-phenoxy)-, -(2,6-dichloro-4-trifluoromethyl-phenoxy)-, -(2-chloro-6-fluoro-4-trifluoromethyl-phenoxy)-, -(2,3,6-trichloro-4-trifluoromethyl-phenoxy- and -(2,6-dichloro-3-fluoro-4-trifluoromethyl-phenoxy)-naphthalene-2-sulphonyl chloride.

The compounds of the formula (IX) are the subject-matter of German Patent Application DE-P 3,823,318 of Jul. 9, 1988.

The (hetero)aryloxynaphthalenesulphonyl chlorides of the formula (IX) are obtained when halogeno(-hetero)aryl compounds of the formula (VIII) are reacted with hydroxynaphthalenesulphonic acids of the general formula (X)

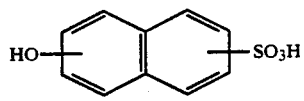

or their metal salts, if appropriate in the presence of an acid acceptor, such as, for example, potassium hydroxide or sodium hydroxide, and, if appropriate, in the presence of a diluent, such as, for example, dimethylformamide, dimethylacetamide, dimethyl sulphoxide, tetramethylene sulphone or N-methylpyrrolidone, at temperatures between 20° C. and 150° C., isolating the (hetero)aryloxynaphthalenesulphonic acids, formed in this process, of the general formula (XI)

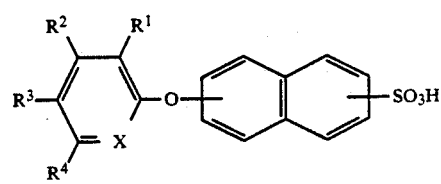

in which $R^1$, $R^2$, $R^3$, $R^4$ and X have the abovementioned meanings, or their metal salts by customary methods, reacting the compounds with a halogenating agent, such as, for example, thionyl chloride, phosgene, phosphorus(V) chloride and/or phosphoryl chloride, if appropriate in the presence of a diluent, such as, for example, methylene chloride, chloroform, tetrachloromethane, chlorobenzene or o-dichlorobenzene, at temperatures between 0° C. and 100° C., and working up is carried out by customary methods.

Examples which may be mentioned of the hydroxynaphthalenesulphonic acids of the formula (IX) and their salts, which are required as starting substances, are: 6-hydroxy-naphthalene-2-sulphonic acid and the sodium and potassium salts thereof, 7-hydroxy-naphthalene-2-sulphonic acid and the sodium and potassium salts thereof, 7-hydroxy-naphthalene-1-sulphonic acid and the sodium and potassium salts thereof, 6-hydroxy-naphthalene-1-sulphonic acid and the sodium and potassium salts thereof and 5-hydroxy-naphthalene-1-sulphonic acid and the sodium and potassium salts thereof.

The hydroxynaphthalenesulphonic acids of the formula (X) are known chemicals for organic synthesis.

Formula (III) provides a general definition of the alkylating agents furthermore to be used as starting substances in process (a) for the preparation of compounds of the formula (I).

In formula (III), A, R and Z preferably, or in particular, have those meanings which have already been mentioned above in connection with the description of the compounds of the formula (I) according to the invention as being preferred, or particularly preferred, for A, R and Z, and $X^1$ preferably represents chlorine or bromine.

Examples of the starting substances of the formula (III) are listed in Table 2 below.

(III)

TABLE 2

Examples of the starting substances of the formula (III)

| $X^1$ | A | R | Z |
|---|---|---|---|
| Cl | CH$_2$ | CH$_3$ | O |
| Br | CH$_2$ | CH$_3$ | O |
| Cl | CH$_2$ | C$_2$H$_5$ | O |
| Cl | CH$_2$ | C$_3$H$_7$ | O |
| Cl | CH$_2$ | CH(CH$_3$)$_2$ | O |
| Cl | CH$_2$ | C$_4$H$_9$ | O |
| Cl | CH$_2$ | C(CH$_3$)$_3$ | O |
| Cl | CH$_2$CH$_2$ | CH$_3$ | O |
| Cl | CH$_2$CH$_2$ | C(CH$_3$)$_3$ | O |
| Cl | CHCH$_3$ | CH$_3$ | O |
| Cl | CHCH$_3$ | C$_2$H$_5$ | O |
| Cl | CH$_2$ | CH$_3$ | NCH$_3$ |
| Cl | CH$_2$ | CH$_3$ | NC$_2$H$_5$ |
| Cl | CH$_2$ | CH$_3$ | NC$_3$H$_7$ |
| Cl | CH$_2$ | CH$_3$ | NCH(CH$_3$)$_2$ |
| Cl | CH$_2$ | CH$_3$ | NC$_4$H$_9$ |
| Cl | CH$_2$ | CH$_3$ | NOCH$_3$ |
| Cl | CH$_2$ | CH$_3$ | NOC$_2$H$_5$ |
| Cl | CH$_2$ | CH$_3$ | NOC$_3$H$_7$ |
| Cl | CH$_2$ | CH$_3$ | NOCH(CH$_3$)$_2$ |
| Cl | CH$_2$ | CH$_3$ | NOC$_4$H$_9$ |
| Cl | CH$_2$ | CH$_3$ | NOCH$_2$CH(CH$_3$)$_2$ |
| Cl | CH$_2$ | CH$_3$ | NN(CH$_3$)$_2$ |
| Cl | CH$_2$ | CH$_3$ | NNHCH$_3$ |
| Cl | CH$_2$ | CH$_3$ | NNHC$_2$H$_5$ |
| Cl | CH$_2$ | CH$_3$ | NNHC$_3$H$_7$ |
| Cl | CH$_2$ | CH$_3$ | NNHCH(CH$_3$)$_2$ |
| Cl | CH$_2$ | CH$_3$ | NNHC$_4$H$_9$ |
| Cl | CH$_2$ | CH$_3$ | NNHC(CH$_3$)$_3$ |
| Cl | CH$_2$ | CH$_3$ | NCH$_2$COOCH$_3$ |
| Cl | CH$_2$ | CH$_3$ | NCH$_2$COOC$_2$H$_5$ |
| Cl | CH$_2$ | CH$_3$ | NCHCOOCH$_3$<br>\|<br>CH$_3$ |
| Cl | CH$_2$ | CH$_3$ | NCHCOOC$_2$H$_5$<br>\|<br>CH$_3$ |

The starting substances of the formula (III) are known and/or can be prepared by processes which are known per se (cf. Org. Prep. Proced. Int. 11 (1979), 115 et seq.; loc. cit. 12 (1980), 49 et seq. Synthesis 1982, 43 et seq.).

Process (a) according to the invention for the preparation of the novel compounds of the formula (I) is preferably carried out using diluents. Suitable diluents in this context are virtually all inert organic solvents. These preferably include aliphatic and aromatic, optionally halogenated hydrocarbons, such as pentane, hexane, heptane, yyclohexane, petroleum ether, benzine, ligroin, benzene, toluene, xylene, methylene chloride, ethylene chloride, chloroform, carbon tetrachoride, chlorobenzene and o-dichlorobenzene, ethers, such as diethyl ether and dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide and N-methyl-pyrrolidone, and also dimethyl sulphoxide, tetramethylene sulphone and hexamethylphosphoric triamide.

Particularly preferred solvents are aprotic polar organic solvents, such as, for example, acetone, acetonitrile, methyl ethyl ketone, propionitrile, dimethylformamide, dimethylacetamide, dimethyl sulphoxide, sulpholane and N-methylpyrrolidone.

Acid acceptors which can be employed in process (a) according to the invention are all acid-binding agents which can customarily be employed for reactions of this type. Alkali metal hydroxides, such as, for example, sodium hydroxide and potassium hydroxide, alkaline earth metal hydroxides, such as, for example, calcium hydroxide, alkali metal carbonates and alkali metal alkoxides, such as sodium carbonate and potassium carbonate, sodium tert-butoxide and potassium tert-butoxide, furthermore aliphatic, aromatic or heterocyclic amines, for example triethylamine, trimethylamine, dimethylaniline, dimethylbenzylamine, pyridine,1,5-diazabicyclo-[4,3,0]-non-5-ene (DBN), 1,8-diazabicyclo-[5,4,0]-undec-7-ene (DBU) and 1,4-diazabicyclo-[2,2,2]-octane (DABCO) are preferably suitable.

In process (a) according to the invention, the reaction temperatures can be varied within a relatively wide range. In general, the reaction is carried out at temperatures between 0° C. and 200° C., preferably at temperatures between 20° C. and 150° C.

Process (a) according to the invention is generally carried out under atmospheric pressure. However, it is also possible to carry out the process under increased or reduced pressure.

For carrying out process (a) according to the invention, the specific starting substances required are generally employed in approximately equimolar amounts. However, it is also possible to use one of the two components employed in each case in a relatively large excess. In general, the reactions are carried out in a suitable diluent in the presence of an acid acceptor, and the reaction mixture is stirred for several hours at the specific temperature required. Working-up in process (a) according to the invention is carried out in each case by customary methods.

Formula (Ia) provides a general definition of the carbonyl compounds to be used as starting substances in process (b) according to the invention for the preparation of compounds of the formula (I).

In formula (Ia), A, R, $R^1$, $R^2$, $R^3$, $R^4$, X and Y preferably, or in particular, have those meanings which have already been mentioned above in connection with the description of the compounds of the formula (I) according to the invention as being preferred, or particularly preferred, for A, R, $R^1$, $R^2$, $R^3$, $R^4$, X and Y.

Examples of the starting substances of the formula (Ia) are listed in Table 3 below.

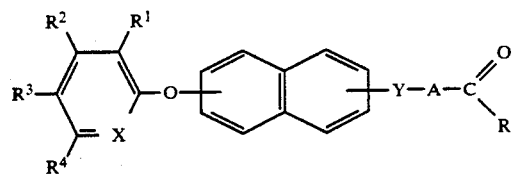

TABLE 3

| | | | Examples of the starting substances of the formula (Ia) | | | | |
|---|---|---|---|---|---|---|---|
| $R^1$ | $R^2$ | $R^3$ | $R^4$ | X | Y | A | R |
| Cl | H | Cl | H | CH | O | $CH_2$ | $CH_3$ |
| Cl | H | Cl | H | CH | S | $CH_2$ | $CH_3$ |
| Cl | H | Cl | H | N | O | $CH_2$ | $CH_3$ |
| Cl | H | Cl | H | N | S | $CH_2$ | $CH_3$ |
| Cl | H | $CF_3$ | H | CH | O | $CH_2$ | $CH_3$ |
| Cl | H | $CF_3$ | H | CH | S | $CH_2$ | $CH_3$ |
| Cl | H | $CF_3$ | H | N | O | $CH_2$ | $CH_3$ |
| Cl | H | $CF_3$ | H | N | S | $CH_2$ | $CH_3$ |
| Cl | H | $CF_3$ | H | C—Cl | O | $CH_2$ | $CH_3$ |
| Cl | H | $CF_3$ | H | C—Cl | S | $CH_2$ | $CH_3$ |
| Cl | H | $CF_3$ | H | C—F | O | $CH_2$ | $CH_3$ |
| Cl | H | $CF_3$ | H | C—F | S | $CH_2$ | $CH_3$ |
| Cl | H | $CF_3$ | F | C—Cl | O | $CH_2$ | $CH_3$ |
| Cl | H | $CF_3$ | F | C—Cl | S | $CH_2$ | $CH_3$ |
| Cl | H | $CF_3$ | Cl | C—Cl | S | $CH_2$ | $CH_3$ |
| Cl | H | $CF_3$ | Cl | C—Cl | O | $CH_2$ | $CH_3$ |
| CN | H | $CF_3$ | H | CH | O | $CH_2$ | $CH_3$ |
| Cl | H | $SO_2CF_3$ | H | CH | O | $CH_2$ | $CH_3$ |
| Cl | H | $SO_2CF_3$ | H | C—Cl | O | $CH_2$ | $CH_3$ |
| F | H | $CF_3$ | H | C—F | O | $CH_2$ | $CH_3$ |
| Cl | H | Cl | H | N | O | $CH_2$ | $C_2H_5$ |
| Cl | H | $CF_3$ | H | C—Cl | O | $CH_2$ | $C_2H_5$ |
| Cl | H | $CF_3$ | H | C—F | O | $CH_2$ | $C_2H_5$ |
| Cl | H | $CF_3$ | H | C—F | O | $CH_2$ | $CH(CH_3)_2$ |
| Cl | H | $CF_3$ | H | C—Cl | O | $CH_2$ | $C(CH_3)_3$ |
| Cl | H | $CF_3$ | H | C—F | O | $CH_2$ | $C(CH_3)_3$ |
| Cl | H | $CF_3$ | H | N | O | $CH_2CH_2$ | $CH_3$ |
| Cl | H | $CF_3$ | H | CH | O | $CHCH_3$ | $CH_3$ |
| Cl | H | Cl | H | N | O | $CHCH_3$ | $C_2H_5$ |
| Cl | H | $CF_3$ | H | C—Cl | O | $CH_2$ | $CH_2Cl$ |
| Cl | H | $CF_3$ | H | C—Cl | O | $CH_2$ | $CF_3$ |
| Cl | H | Cl | H | N | O | $CH_2$ | $CF_3$ |
| Cl | H | Cl | H | N | O | $CH_2$ | $CH_2Cl$ |

The individual examples indicated in Table 3 in each case hold for the very particularly preferred groups of compounds of the formula (I) which are outlined above by the formulae (IA), (IB), (IC), (ID) and (IE).

The starting substances of the formula (Ia) for process (b) according to the invention are novel compounds according to the invention; they can be prepared by process (a) according to the invention.

Formulae (IV) and (V) provide general definitions of the amino compounds furthermore to be employed as starting substances in process (b) according to the invention. In formulae (IV) and (V), n, $R^6$, $R^7$ and $R^8$ preferably, or in particular, have those meanings which have already been mentioned above in connection with the description of the compounds of the formula (I) according to the invention as being preferred, or particularly preferred, for n, $R^6$, $R^7$ and $R^8$.

Examples which may be mentioned of the starting substances of the formulae (IV) and (V) are: ammonia, methylamine, ethylamine, propylamine, isopropylamine, butylamine, isobutylamine, sec-butylamine, tert-butylamine, allylamine, methyl aminoacetate and ethyl aminoacetate, methyl α-aminopropionate and ethyl α-aminopropionate, benzylamine, 2-fluoro-, 3-fluoro- and 4-fluoro-benzylamine, 2-chloro-, 3-chloro- and 4-chlorobenzylamine, 2-methyl-, 3-methyl- and 4-methyl-benzylamine, 4-methoxy-benzylamine, 3,4-dimethyl- and 3,4-dimethoxy-benzylamine, hydroxylamine, O-methyl-, O-ethyl-O-propyl, O-isopropyl-, O-butyl-, O-isobutyl-, O-sec-butyl-, O-allyl-, O-benzyl-, O-(2-fluoro-benzyl)-, O-(4-fluoro-benzyl)-, O-(2-chloro-benzyl)-, O-(4-chloro-benzyl)-, O-(2-methyl-benzyl)-, O-(3-methyl-benzyl)-, O-(4-methyl-benzyl)-, O-(3,4-dimethyl-benzyl)-, O-(4-methoxy-benzyl)-, O-(3,4-dimethoxy-benzyl)-, O-(4-methoxycarbonyl-benzyl)- and O-(4-ethoxycarbonyl-benzyl)hydroxylamine, methyl-, ethyl-, propyl- and isopropylaminooxyacetate, N-methyl-, N-ethyl-, N-propyl-, N-isopropyl-, N-dimethyl- and N-diethyl-aminooxyacetamide and N-methyl-aminooxyacetanilide, methyl, ethyl, propyl and isopropyl α-aminooxy-propionate, N-methyl-, N-ethyl-, N-propyl-, N-isopropyl-, N-dimethyl- and N-diethyl-α-aminooxypropionamide and N-methyl-α-aminooxypropionanilide, hydrazine, methylhydrazine, N,N-dimethylhydrazine, ethylhydrazine, propylhydrazine, isopropylhydrazine, butylhydrazine, isobutylhydrazine, sec-butylhydrazine, tert-butylhydrazine, phenylhydrazine, 4-fluoro-, 4-chloro-, 4-bromo-, 4-methyl-, 4-trifluoromethyl- and 4-methoxy-phenylhydrazine, acethydrazide, methyl hydrazinoformate and ethyl hydrazinoformate, methanesulphonyl hydrazide, benzenesulphonyl hydrazide and p-toluenesulphonyl hydrazide.

The amino compounds of the formulae (IV) and (V) are known chemicals for organic synthesis.

Process (b) according to the invention is preferably carried out using diluents. Suitable diluents are those organic solvents which have been mentioned above in the description of process (a) according to the invention, with the exception of ketones. Particularly preferred solvents are those which are suitable for azeotropic water separation, such as, for example, benzene, toluene or xylene.

Process (b) according to the invention is preferably carried out in the presence of a catalyst. Preferred catalysts are strong acids, such as, for example, sulphuric acid, methanesulphonic acid, benzenesulphonic acid or p-toluenesulphonic acid, or ion-exchanger resins which have been activated with acids.

In process (b) according to the invention, the reaction temperatures can be varied within a relatively wide range. In general, the reaction is carried out at temperatures between 0° C. and 200° C., preferably at temperatures between 20° C. and 150° C.

Process (b) according to the invention is generally carried out under atmospheric pressure. However, it is also possible to carry out the process under increased or reduced pressure.

For carrying out process (b) according to the invention, the specific starting substances required are generally employed in approximately equimolar amounts. However, it is also possible to use one of the two components employed in each case in a relatively large excess. In general, the reactions are carried out in a suitable diluent in the presence of a catalyst, and the reaction mixture is stirred for several hours at the specific temperature required, preferably in a water separator and with heating. Working-up in process (b) according to the invention is carried out in each case by customary methods.

Formula (Ib) provides a general definition of the hydroximino compounds to be used as starting substances in process (c) according to the invention for the preparation of compounds of the formula (I).

In formula (Ib), A, R, $R^1$, $R^2$, $R^3$, $R^4$, X and Y preferably, or in particular, have those meanings which have already been mentioned above in connection with the description of the compounds of the formula (I) according to the invention as being preferred, or particularly preferred, for A, R, $R^1$, $R^2$, $R^3$, $R^4$, X and Y.

Examples of the starting substances of the formula (Ib) are listed in Table 4 below.

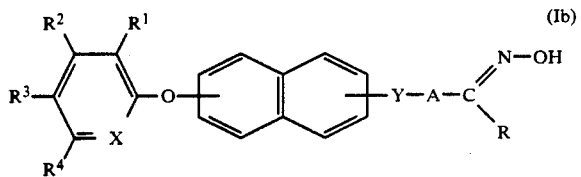

TABLE 4

| Example of the starting substances of the formula (Ib) | | | | | | | |
|---|---|---|---|---|---|---|---|
| $R^1$ | $R^2$ | $R^3$ | $R^4$ | X | Y | A | R |
| Cl | H | Cl | H | CH | O | $CH_2$ | $CH_3$ |
| Cl | H | Cl | H | CH | S | $CH_2$ | $CH_3$ |
| Cl | H | Cl | H | N | O | $CH_2$ | $CH_3$ |
| Cl | H | Cl | H | N | S | $CH_2$ | $CH_3$ |
| Cl | H | $CF_3$ | H | CH | O | $CH_2$ | $CH_3$ |
| Cl | H | $CF_3$ | H | CH | S | $CH_2$ | $CH_3$ |
| Cl | H | $CF_3$ | H | N | O | $CH_2$ | $CH_3$ |
| Cl | H | $CF_3$ | H | N | S | $CH_2$ | $CH_3$ |
| Cl | H | $CF_3$ | H | C—Cl | O | $CH_2$ | $CH_3$ |
| Cl | H | $CF_3$ | H | C—Cl | S | $CH_2$ | $CH_3$ |
| Cl | H | $CF_3$ | H | C—F | O | $CH_2$ | $CH_3$ |
| Cl | H | $CF_3$ | H | C—F | S | $CH_2$ | $CH_3$ |
| Cl | H | $CF_3$ | F | C—Cl | O | $CH_2$ | $CH_3$ |
| Cl | H | $CF_3$ | F | C—Cl | S | $CH_2$ | $CH_3$ |
| Cl | H | $CF_3$ | Cl | C—Cl | S | $CH_2$ | $CH_3$ |
| Cl | H | $CF_3$ | Cl | C—Cl | O | $CH_2$ | $CH_3$ |
| CN | H | $CF_3$ | H | CH | O | $CH_2$ | $CH_3$ |
| Cl | H | $SO_2CF_3$ | H | CH | O | $CH_2$ | $CH_3$ |
| Cl | H | $SO_2CF_3$ | H | C—Cl | O | $CH_2$ | $CH_3$ |
| F | H | $CF_3$ | H | C—F | O | $CH_2$ | $CH_3$ |
| Cl | H | Cl | H | N | O | $CH_2$ | $C_2H_5$ |
| Cl | H | $CF_3$ | H | C—Cl | O | $CH_2$ | $C_2H_5$ |
| Cl | H | $CF_3$ | H | C—F | O | $CH_2$ | $C_2H_5$ |
| Cl | H | $CF_3$ | H | C—F | O | $CH_2$ | $CH(CH_3)_2$ |
| Cl | H | $CF_3$ | H | C—Cl | O | $CH_2$ | $C(CH_3)_3$ |
| Cl | H | $CF_3$ | H | C—F | O | $CH_2$ | $C(CH_3)_3$ |
| Cl | H | $CF_3$ | H | N | O | $CH_2CH_2$ | $CH_3$ |

TABLE 4-continued

| Example of the starting substances of the formula (Ib) | | | | | | | |
|---|---|---|---|---|---|---|---|
| $R^1$ | $R^2$ | $R^3$ | $R^4$ | X | Y | A | R |
| Cl | H | $CF_3$ | H | CH | O | $CHCH_3$ | $CH_3$ |
| Cl | H | Cl | H | N | O | $CHCH_3$ | $C_2H_5$ |
| Cl | H | $CF_3$ | H | C—Cl | O | $CH_2$ | $CH_2Cl$ |
| Cl | H | $CF_3$ | H | C—Cl | O | $CH_2$ | $CF_3$ |
| Cl | H | Cl | H | N | O | $CH_2$ | $CF_3$ |
| Cl | H | Cl | H | N | O | $CH_2$ | $CH_2Cl$ |

The individual examples indicated in Table 4 in each case hold for the very particularly preferred groups of compounds of the formula (I) which are outlined above by the formulae (IA), (IB), (IC), (ID) and (IE).

The starting substances of the formula (Ib) for process (c) according to the invention are novel compounds according to the invention; they can be prepared by processes (a) and (b) according to the invention.

Formula (VI) provides a general definition of the alkylating agents furthermore to be used as starting substances in process (c) according to the invention for the preparation of compounds of the formula (I).

In formula (VI), $R^6$ preferably, or in particular, has the meaning which has already been indicated above in connection with the description of the compounds of the formula (I) according to the invention as being preferred, or particularly preferred, for $R^6$, and $X^2$ preferably represents chlorine, bromine, iodine, methylsulphonyl, phenylsulphonyl or p-toluenesulphonyl.

Examples which may be mentioned of the starting substances of the formula (VI) are: chloro-, bromo- or iodo-methane, -ethane, -propane, -butane, the methyl and ethyl esters of chloro-, bromo- or iodo-acetic acid, N-dimethyl- and N-diethyl-chloroacetamide, -bromoacetamide and -iodoacetamide, N-methyl-chloroacetanilide, -bromoacetanilide and -iodoacetanilide, allyl bromide, benzyl chloride, 2-fluoro-benzyl chloride, 4-fluoro-benzyl chloride, 4-chloro-benzyl chloride, 4-methyl-benzyl chloride and 4-methoxy-benzyl chloride, 2-bromo-propane, the methyl and ethyl esters of α-bromo- and α-chloro-propionic acid, N-methyl-α-bromopropionamide and -α-chloropropionamide, N-ethyl-α-bromopropionamide and -α-chloropropionamide, N-diethyl-α-bromopropionamide and -α-chloropropionamide, N-diethyl-α-bromopropionamide and -α-chloropropionamide, N-methyl-α-bromopropionanilide and -α-chloropropionanilide.

The starting substances of the formula (VI) are known chemicals for organic synthesis.

Process (c) according to the invention is preferably carried out using diluents. Suitable diluents are mainly those organic diluents which have been mentioned above in the description of process (a) according to the invention.

Process (c) according to the invention is preferably carried out in the presence of an acid acceptor. Suitable acid acceptors are mainly those acid-binding agents which have been mentioned above in the description of process (a) according to the invention.

In process (c) according to the invention, the reaction temperatures can be varied within a relatively wide range. In general, the process is carried out at temperatures between 0° C. and 150° C., preferably at temperatures between 10° C. and 100° C.

For carrying out process (c) according to the invention, the specific starting substances required are generally employed in approximately equimolar amounts. However, it is also possible to use one of the two components employed in each case in a relatively large excess. In general, the reactions are carried out in a suitable diluent in the presence of an acid acceptor, and the reaction mixture is stirred for several hours at the specific temperature required. Working-up in process (c) according to the invention is in each case carried out by customary methods.

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alpecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds of the formula (I) according to the invention can be used with particularly good success for selectively combating dicotyledon weeds in monocotyledon and dicotyledon cultures, such as cereals, corn, rice and soy.

The active compounds can be converted to the customary formulations, such as solutions, emulsions, wettable powders, suspensions, powders, dusting agents, pastes, soluble powders, granules, suspension emulsion concentrates, natural and synthetic materials impregnated with active compound, and very fine capsules in polymeric substances.

These formulations are produced in known manner, for example by mixing the active compounds with extenders, that is, liquid solvents and/or solid carriers, optionally with the use of surface-active agents, that is, emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly-disperse silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolyzates; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids can be used in the formulations. Further additives may be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

When used as herbicides, the active compounds according to the invention, as such or in the form of their formulations, can also be used, for combating weeds, as mixtures with known herbicides, finished formulations or tank mixes being possible.

Suitable components for the mixtures are known herbicides, such as, for example, 1-amino-6-ethylthio-3,-(2,2-dimethylpropyl)-1,3,5-triazine-2,4(1H,3H)-dione (AMETHYDIONE) or N-(2-benzothiazolyl)-N,N'-dimethyl-urea (METABENZTHIAZURON) for combating weeds in cereals; 4-amino-3-methyl-6-phenyl-1,2,4-triazin-5(4H)-one (METAMITRON) for combating weeds in sugar beets and 4-amino-6-(1,1-dimethylethyl)-3-methylthio-1,2,4-triazin-5(4H)-one (METRIBUZIN) for combating weeds in soy beans. 2,4-Dichlorophenoxyacetic acid (2,4-D); 4-(2,4-dichlorophenoxy)-butyric acid (2,4-DB); 2,4-dichlorophenoxypropionic acid (2,4-DP); 5-(2-chloro-4-trifluoromethyl-phenoxy)-2-nitrobenzoic acid (ACIFLUORFEN); 2-chloro-4-ethylamino-6 -isopropylamino-1,3,5-triazine (ATRAZIN); methyl 2-[[[[(4,6-dimethoxypyrimidin-2-yl)-amino]-carbonyl]-amino]-sulphonyl]-methyl]-benzoate (BENSULFURON); 3-isopropyl-2,1,3-benzothiadiazin-4-one 2,2-dioxide (BENTAZONE); methyl 5-(2,4-dichlorophenoxy)-2-nitrobenzoate (BIFENOX); 3,5-dibromo-4-hydroxy-benzonitrile (BROMOXYNIL); ethyl 2-{[(4-chloro-6-methoxy-2-pyrimidinyl)-aminocarbonyl]-aminosulphonyl}-benzoate (CHLORIMURON); 2-chloro-N-{[(4-methoxy-6-methyl-1,3,5-triazin-2-yl)-amino]-carbonyl}-benzenesulphonamide (CHLORSULFURON); N,N-dimethyl-N'-(3-chloro-4-methylphenyl)-urea (CHLORTOLURON); exo-1-methyl-4-(1-methyl-ethyl)-2-(2-methylphenyl-methoxy)-7-oxabicyclo-(2,2,1)-HEPTANE (CINMETHYLIN); 2-chloro-4-ethylamino-6-(3-cyano-propylamino)-1,3,5-triazine (CYANAZIN); 2,6-dichlorobenzonitrile (DICHLOBENIL); 2-[4-(2,4-dichlorophenoxy)-phenoxy]-propionic acid, the methyl or the ethyl ester thereof (DICLOFOP); 2-[(2-chloro-phenyl)-methyl]-4,4-dimethyl-isoxazolidin-3-one [DIMETHAZONE); 2-{4-[(6-chloro-2-benzoxazol-yl)-oxy]-phenoxy}-propanoic acid, the methyl or the ethyl ester thereof (FENOXAPROP); 2-[4-(5-trifluoromethyl-2-pyridyloxy)-phenoxy]-propanoic acid or the butyl ester thereof (FLUAZIFOP); N,N-dimethyl-N'-(3-trifluoromethylphenyl)-urea (FLUOMETURON); 1-methyl-3-phenyl-5-(3-trifluoromethylphenyl)-4-pyridone (FLURIDONE); [(4-amino-3,5-dichloro-6-fluoro-2-pyridinyl)-oxy]-acetic acid or the 1-methylheptyl ester thereof (FLUROXYPYR); 5-(2-chloro-4-trifluoromethyl-phenoxy)-N-methylsulphonyl-2-nitrobenzamide (FOMESAFEN); N-phosphonomethyl-glycine (GLYPHOSATE); 2-{4-[(3-chloro-5-(trifluoromethyl)-2-pyridinyl)-oxy]-phenoxy}-propanoic acid or the ethyl ester thereof (HALOXYFOP); methyl 2-[4,5-dihydro-4-methyl-4-(1-methylethyl)-5-oxo-1H-imidazol-2-yl]-4(5)-methylbenzoate(IMAZAMETHABENZ); 2-(4,5-dihydro-4-methyl-4-isopropyl-5-oxo-1H-imidazol-2-yl)-pyridine-3-carboxylic acid (IMAZAPYR); 2-[5-methyl-5-(1-methylethyl)-4-oxo-2-imidazolin-2-yl]-3-quinolinecarboxylic acid (IMAZAQUIN); 2-[4,5-dihydro-4-methyl-4-isopropyl-5-oxo-(1H)-imidazol-2-yl]-5-ethyl-pyridine-3-carboxylic acid (IMAZETHAPYR); 3,5-diiodo-4-hydroxybenzonitrile (IOXYNIL); N,N-dimethyl-N'-(4-isopropylphenyl)-urea (ISOPROTURON);2-ethoxy-1-methyl-2-oxo-ethyl 5-[2-chloro-4-(trifluoromethyl)-phenoxy]-2-nitrobenzoate (LACTOFEN); (2-methyl-4-chlorophenoxy)-acetic acid (MCPA); (4-chloro-2-methylphenoxy)-propionic acid (MCPP); 2-{[[((4-methoxy-6-methyl-1,3,5-triazin-2-yl)-amino)-carbonyl]-amino]-sulphonyl}-benzoic acid or the methyl ester thereof (METSULFURON);2-chloro-4-trifluoromethylphenyl 3-ethoxy-4-nitro-phenyl ether (OXYFLUORFEN); O-(6-chloro-3-phenyl-pyridazin-4-yl) S-octyl thiocarbonate (PYRIDATE); 2-chloro-4,6-bis(ethylamino)-1,3,5-triazine(-SIMAZIN);2,4-bis-[N-ethylamino]-6-methylthio-1,3,5-triazine (SIMETRYNE); methyl 2-{[(4,6-dimethyl-2-pyrimidinyl)-aminocarbonyl]-aminosulphonyl}-benzoate (SULFOMETURON); 4-ethylamino-2-t-butylamino-6-methylthio-s-triazine (TERBUTRYNE); methyl 3-[[[[(4-methoxy-6-methyl-1,3,5-triazin-2-yl)-amino]-carbonyl]-amino]-sulophonyl]-thiophene-2-carboxylate (THIAMETURON); some mixtures surprisingly also exhibit a synergistic effect.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5.0 kg per ha.

The preparation and the use of the active substances according to the invention can be seen from the examples below.

PREPARATION EXAMPLES

EXAMPLE 1

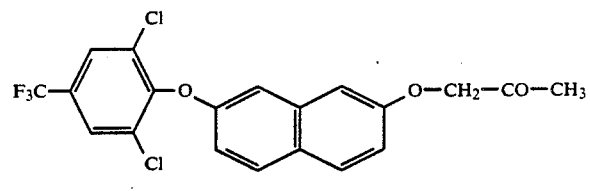

A mixture of 1.9 g (5.0 mol) of 7-(2,6-dichloro-4-trifluoromethyl-phenoxy)-2-naphthol, 0.5 g (6.0 mmol) of chloroacetone, 0.8 g (6.0 mmol) of potassium carbonate and 50 ml of acetonitrile is refluxed for 5 hours and then stirred at 20° C. for 15 hours. The mixture is subsequently diluted with water to approximately twice the volume, and the product which is obtained in this process in the form of crystals is isolated by filtering off with suction.

2.0 g (93% of theory) of (7-(2,6-dichloro-4-trifluoromethyl-phenoxy)-naphthalen-2-yl-oxy)-acetone of melting point 132° C. are obtained.

EXAMPLE 2

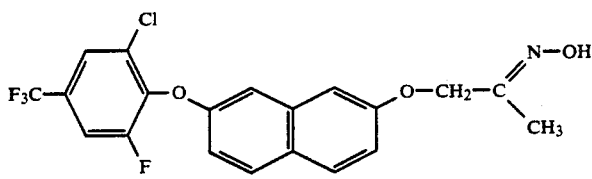

A mixture of 24.8 g (0.06 mol) of (7-(2-chloro-6-fluoro-4-trifluoromethyl-phenoxy)-naphthalen-2-yl-oxy)-acetone, 4.8 g (0.06 mol) of hydroxylamine hydrochloride, 6.0 g (0.06 mol) of triethylamine and 500 ml of toluene is refluxed for 15 hours. After the mixture has cooled to 20° C., it is washed with water and the organic phase is dried using sodium sulphate and filtered. The filtrate is concentrated, the product remaining in the residue is brought to crystallization by trituration with ethanol/hexane and isolated by filtering off with suction.

18.4 g (72% of theory) of (7-(2-chloro-6-fluoro-4-trifluoromethyl-phenoxy)-naphthalen-2-yl-oxy)-acetoneoxime (E/Z=7/3) of melting point 153° C. are obtained.

EXAMPLE 3

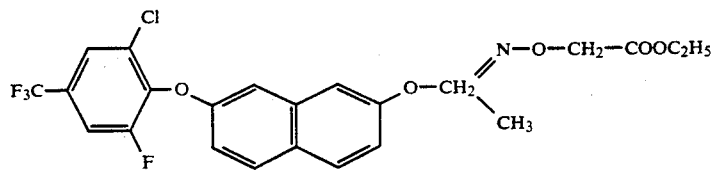

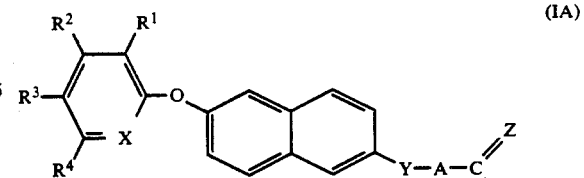

(IA)

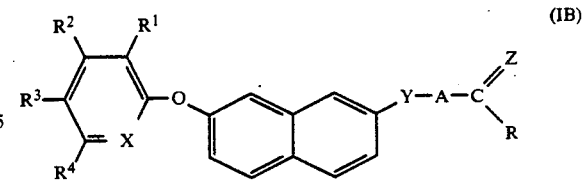

(IB)

A mixture of 8.6 g (0.02 mol) of (7-(2-chloro-6-fluoro-4-trifluoromethyl-phenoxy)-naphthalen-2-yl-oxy)-acetoneoxime (E/Z=7/3), 3.5 g (0.021 mol) of ethyl bromoacetate, 3.2 g (0.023 mol) of potassium carbonate and 100 ml of acetonitrile is refluxed for 20 hours and subsequently concentrated The residue is taken up in ethyl acetate, and the mixture is washed with water, dried using sodium sulphate and filtered The filtrate is concentrated, the residue is stirred with methanol, and the product which is obtained in this process in the form of crystals is isolated by filtering off with suction.

9.6 g (93% of theory) of 7-(2-chloro-6-fluoro-4-trifluoromethyl-phenoxy)-2-(2-ethoxycarbonylmethoximinopropoxy)-naphthalene (E/Z=7/3) of melting point 109° C. are obtained.

The compounds of the formula (I)—which are specified in more detail by the "isomer groups" of the formulae (IA), (IB), (IC), (ID) and (IE) and which are listed in Table 5 below—can be prepared in analogy to Examples 1 to 3 and in accordance with the general description of the preparation processes according to the invention.

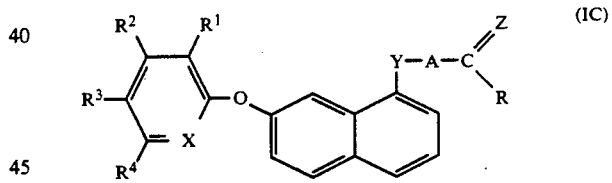

(IC)

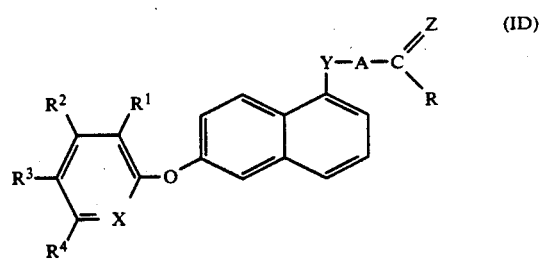

(ID)

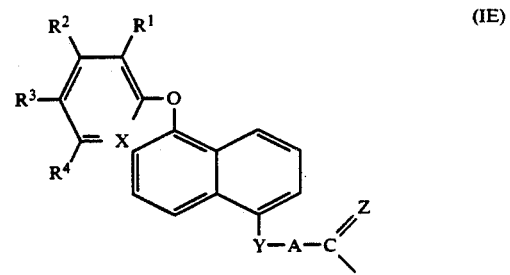

(IE)

TABLE 5

Examples of the compounds of the formula (I)

| Example No. | Isomer group | $R^1$ | $R^2$ | $R^3$ | $R^4$ | X | Y | A | R | Z | Physical data |
|---|---|---|---|---|---|---|---|---|---|---|---|
| 4 | IA | Cl | H | $CF_3$ | H | C—Cl | O | $CH_2$ | $CH_3$ | O | mp: 147° C. |
| 5 | IA | Cl | H | $CF_3$ | H | C—Cl | O | $CH_2$ | $CH_3$ | N—OH (E/Z = 4/1) | mp: 163° C. |
| 6 | IB | Cl | H | $CF_3$ | H | C—Cl | O | $CH_2$ | $CH_3$ | N—OH (E/Z = 1/1) | mp: 180° C. |
| 7 | IB | Cl | H | $CF_3$ | H | C—Cl | O | $CH_2$ | $CH_3$ | N—OH (E/Z = 99/1) | mp: 147° C. |
| 8 | IB | Cl | H | $CF_3$ | H | C—Cl | O | $CH_2$ | $CH_3$ | N—$OCH_3$ (E/Z = 3/1) | |
| 9 | IB | Cl | H | $CF_3$ | H | C—Cl | O | $CH_2$ | $CH_3$ | N—O—$CH_2$—N($CH_3$)($C_6H_5$) (E/Z = 2/1) | mp: 114° C. |
| 10 | IA | Cl | H | $CF_3$ | H | C—Cl | O | $CH_2$ | $CH_3$ | N—O—$CH_2$—$COOC_2H_5$ (E/Z = 7/3) | mp: 98° C. |
| 11 | IB | Cl | H | $CF_3$ | H | C—Cl | O | $CH_2$ | $CH_3$ | N—O—$CH_2$—$COOC_2H_5$ (E/Z = 7/3) | mp: 119° C. |
| 12 | IA | Cl | H | $CF_3$ | H | C—Cl | O | $CH_2$ | $CH_3$ | N—$OCH_3$ (E/Z = 99/1) | mp: 117° C. |
| 13 | IA | Cl | H | $CF_3$ | H | C—Cl | O | $CH_2$ | $CH_3$ | N—O—$CH_2$—CO—N($CH_3$)($C_6H_5$) (E/Z = 8/2) | mp: 165° C. |
| 14 | IB | Cl | H | $CF_3$ | H | C—F | O | $CH_2$ | $CH_3$ | O | mp: 94° C. |
| 15 | IB | Cl | H | $CF_3$ | H | C—F | O | $CH_2$ | $CH_3$ | N—O—CH($CH_3$)—$COOC_2H_5$ | |
| 16 | IB | Cl | H | $CF_3$ | H | C—Cl | S | $CH_2$ | $CH_3$ | N—O—$CH_2$—$COOC_2H_5$ | |
| 17 | IB | Cl | H | $CF_3$ | H | C—Cl | O | $CH_2$ | $CH_3$ | N—$CH_2$—$COOC_2H_5$ | |
| 18 | IB | Cl | H | $CF_3$ | H | C—Cl | O | $CH_2$ | $CH_3$ | N—O—$CH_2$—$COOCH_3$ | |
| 19 | IB | Cl | H | $CF_3$ | H | C—Cl | S | $CH_2$ | $CH_3$ | N—O—$CH_2$—$COOCH_3$ | |
| 20 | IB | Cl | H | $CF_3$ | H | C—Cl | O | $CH_2$ | H | N—O—$CH_2$—$COOC_2H_5$ | |
| 21 | IB | Cl | H | $CF_3$ | H | C—Cl | O | $CH_2$ | H | N—O—$CH_2$—$COOCH_3$ | |
| 22 | IB | Cl | H | $CF_3$ | H | C—F | S | $CH_2$ | $CH_3$ | N—O—$CH_2$—$COOCH_3$ | |
| 23 | IB | Cl | H | $CF_3$ | H | C—F | O | $CH_2$ | $CH_3$ | N—CH($CH_3$)—$COOC_2H_5$ | |
| 24 | IB | Cl | H | $CF_3$ | H | N | O | $CH_2$ | $CH_3$ | N—$CH_2$—$COOC_3H_7$ | |
| 25 | IB | Cl | H | $CF_3$ | H | N | O | $CH_2$ | $CH_3$ | N—O—$CH_2$—$COOCH(CH_3)_2$ | |
| 26 | IB | Cl | H | $CF_3$ | H | C—Cl | O | $CH_2$ | $CH_3$ | O | |
| 27 | IB | Cl | H | $CF_3$ | H | C—F | O | $CH_2$ | $CH_3$ | O | |
| 28 | IB | Cl | H | $CF_3$ | H | C—Cl | S | $CH_2$ | $CH_3$ | O | |
| 29 | IA | Cl | H | $CF_3$ | H | C—F | O | $CH_2$ | $CH_3$ | N—$CH_2$—$COOC_2H_5$ | |
| 30 | IB | Cl | H | $CF_3$ | H | C—F | O | $CH_2$ | $CH_3$ | N—$CH_2$—$COOC_2H_5$ | |
| 31 | IB | Cl | H | $CF_3$ | H | C—Cl | O | $CH_2$ | $CH_3$ | N—$NH_2$ | mp: 163° C. |
| 32 | IB | Cl | H | $CF_3$ | H | C—Cl | O | $CH_2$ | $CH_3$ | N—$NHCH_2COOC_2H_5$ | (amorphous) |
| 33 | IB | Cl | H | $CF_3$ | H | N | O | $CH_2$ | $CH_3$ | O | mp: 150° C. |
| 34 | IB | Cl | H | $CF_3$ | H | C—F | S | $CH_2$ | $CH_3$ | O | mp: 102° C. |
| 35 | IB | Cl | H | $CF_3$ | H | N | O | $CH_2$ | $CH_3$ | N—OH | mp: 128° C. |
| 36 | IB | Cl | H | $CF_3$ | H | N | O | $CH_2$ | $CH_3$ | N—$OCH_2COOCH_3$ | |
| 37 | IB | Cl | H | $CF_3$ | H | C—F | S | $CH_2$ | $CH_3$ | N—OH | |
| 38 | IB | Cl | H | $CF_3$ | H | C—F | S | $CH_2$ | $CH_3$ | $NOCH_2COOCH_3$ | |

STARTING SUBSTANCES OF THE FORMULA (II)

EXAMPLE (II-1)

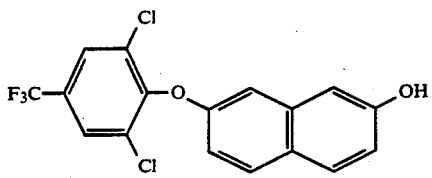

12.5 g (0.05 mol) of 3,4,5-trichloro-benzotrifluoride are added slowly to a stirred mixture, heated to 60° C., of 8.0 g (0.05 mol) of 2,7-dihydroxy-naphthalene, 4.2 g (0.075 mol) of potassium hydroxide powder and 100 ml of dimethyl sulphoxide, and stirring of the reaction mixture is continued for approximately 3 hours at 60° C. After the mixture has cooled to approximately 20° C., it is diluted with water and methylene chloride and filtered. The organic phase is separated from the filtrate, washed with water, dried using sodium sulphate and filtered. The solvent is distilled off from the filtrate under a waterpump vacuum, the residue is stirred with petroleum ether, and the product which is obtained in this process in the form of crystals is isolated by filtering off with suction.

4.9 g (26% of theory) of 7-(2,6-dichloro-4-trifluoromethyl-phenoxy)-2-naphthol of melting point 98° C. are obtained.

EXAMPLE (II-2)

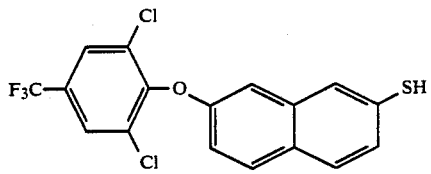

12.5 g (0.025 mol) of 7-(2,6-dichloro-4-trifluoromethylphenoxy)-naphthalene-2-sulphonyl chloride and 25 ml of concentrated hydrochloric acid are added successively to a stirred mixture of 12.5 g (0.19 mol) of zinc dust and 100 ml of dioxane. The reaction mixture is refluxed for 5 hours and then stirred for a further 15 hours at 20° C. After the mixture has been concentrated, the residue is taken up in methylene chloride/water and filtered, the filtrate is shaken, and the organic phase is separated off, washed with water, dried using sodium sulphate and filtered. The filtrate is concentrated, the residue is digested with ethanol, and the product which is obtained in this process in the form of crystals is isolated by filtering off with suction.

4.8 g (49% of theory) of 7-(2,6-dichloro-4-trifluoromethyl-phenoxy)-naphthalene-2-thiol of melting point 98° C. are obtained.

USE EXAMPLES

In the following Use Examples, the compound specified below is used as comparison substance:

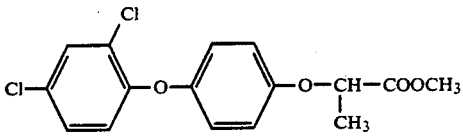

Methyl α-[4-(2,4-dichloro-phenoxy)-phenoxy]-propionate (diclofop-methyl) (disclosed in DE-OS (German Published Specification) 2,223,894/Example 86).

EXAMPLE A

Post-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control.

In this test, for example, the compounds according to Preparation Examples (11) and (14) show a clearly superior activity compared with the prior art.

It is understood that the specification and examples are illustrative but not limitative of the present invention and that other embodiments within the spirit and scope of the invention will suggest themselves to those skilled in the art.

We claim:

1. A disubstituted naphthalene of the formula

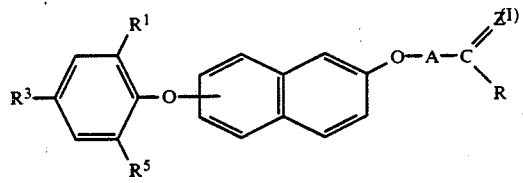

in which
A represents optionally branched $C_1$–$C_4$-alkanediyl,
R represents hydrogen, $C_1$–$C_6$-alkyl or phenyl,
$R^1$ represents fluorine, chlorine, bromine, cyano or trifluoromethyl,
$R^3$ represents fluorine, chlorine, bromine, trifluoromethyl, trifluoromethoxy, trifluoromethylthio or trifluoromethylsulphonyl,
$R^5$ represents fluorine, chlorine or bromine, and
Z represents oxygen, the group $N-(O)_n-R^6$ or

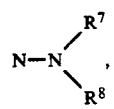

where
n represents the numbers 0 or 1 and $R^6$ represents hydrogen, halogeno-$C_1$-$C_8$-alkyl, or represents $C_1$-$C_8$-alkyl which is optionally substituted by $C_1$-$C_4$-alkoxy, $C_1$-$C_4$-alkylthio, $C_1$-$C_4$-alkylsulphinyl, $C_1$-$C_4$-alkylsulphonyl, carboxyl, $C_1$-$C_4$-alkoxy-carbonyl, $C_1$-$C_4$-alkylamino-carbonyl, di-($C_1$-$C_4$-alkyl)-amino-carbonyl, N-($C_1$-$C_4$-alkyl)-phenylamino-carbonyl or cyano, $C_2$-$C_6$-alkenyl, halogeno-$C_2$-$C_6$-alkenyl, $C_3$-$C_6$-alkinyl, $C_3$-$C_6$-cycloalkyl, $C_3$-$C_6$-cycloalkyl-$C_1$-$C_2$-alkyl, or benzyl, phenylethyl, benzhydryl or phenyl which are in each case optionally substituted in the aromatic moiety by fluorine, chlorine, bromine, cyano, nitro, $C_1$-$C_4$-alkyl, $C_1$-$C_4$-alkoxy and/or $C_1$-$C_4$-alkoxycarbonyl, $R^7$ represents hydrogen or $C_1$-$C_4$-alkyl and $R^8$ represents hydrogen, halogeno-$C_1$-$C_4$-alkyl, or represents $C_1$-$C_4$-alkyl which is optionally substituted by cyano, nitro, $C_1$-$C_4$-alkoxy or $C_1$-$C_4$-alkoxy-carbonyl, $R^8$ further represents $C_3$-$C_6$-alkenyl, $C_3$-$C_6$-alkinyl, $C_3$-$C_6$-cycloalkyl, or represents benzyl, phenylethyl, benzylhydryl or phenyl, which are in each case optionally substituted in the aromatic moiety by fluorine, chlorine, bromine, cyano, nitro, $C_1$-$C_4$-alkyl, trifluoromethyl, $C_1$-$C_4$-alkoxy, difluoromethoxy, trifluoromethoxy, $C_1$-$C_4$-alkylthio, trifluoromethylthio or $C_1$-$C_4$-alkoxy-carbonyl, or is $C_1$-$C_4$-alkyl-carbonyl, $C_1$-$C_4$-alkoxycarbonyl, $C_1$-$C_4$-alkylsulphonyl, or phenylsulphonyl or naphthylsulphonyl, where phenylsulphonyl or naphthylsulphonyl are optionally substituted by fluorine, chlorine, bromine, cyano, nitro, $C_1$-$C_4$-alkyl, trifluoromethyl, $C_1$-$C_4$-alkoxy, difluoromethoxy, trifluoromethoxy, $C_1$-$C_4$-alkylthio, trifluoromethylthio and/or $C_1$-$C_4$-alkoxy-carbonyl, or $R^8$ represents pyrimidinyl.

2. A disubstituted naphthalene according to claim 1, in which

A represents —$CH_2$, —$CH_2CH_2$—, —$CH_2CH_2CH_2$—,

or

R represents methyl, ethyl, propyl, isopropyl, butyl, isobutyl, sec-butyl or tert-butyl, $R^1$ represents fluorine or chlorine, $R^3$ represents chlorine, trifluoromethyl or trifluoromethylsulphonyl, $R^5$ represents fluorine or chlorine, and Z represents oxygen, the group N—(O)$_n$—$R^6$ or

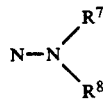

where n represents the numbers 0 or 1 and $R^6$ represents hydrogen, $C_1$-$C_4$-alkyl, $C_3$-$C_4$-alkenyl, $C_1$-$C_3$-alkoxy-carbonyl-$C_1$-$C_2$-alkyl, $C_1$-$C_3$-alkylaminocarbonyl-$C_1$-$C_2$-alkyl, di-($C_1$-$C_3$-alkyl)-amino-carbonyl-$C_1$-$C_2$-alkyl, N-($C_1$-$C_3$-alkyl)-phenylaminocarbonyl-$C_1$-$C_2$-alkyl, or benzyl which is optionally substituted in the aromatic moiety by fluorine, chlorine, methyl, methoxy and/or methoxycarbonyl, $R^7$ represents hydrogen or methyl and $R^8$ represents $C_1$-$C_4$-alkyl, phenyl which is optionally substituted by fluorine, chlorine, bromine, methyl, ethyl, trifluoromethyl, methoxy, ethoxy, difluoromethoxy and/or trifluoromethoxy, or represents acetyl, propionyl, methoxycarbonyl, ethoxycarbonyl, methylsulphonyl, ethylsulphonyl, phenylsulphonyl or tolylsulphonyl.

3. A compound according to claim 1, wherein such compound is 7-(2,6-dichloro-4-trifluoromethyl-phenoxy)-2-(2-ethoxycarbonylmethoximino-propoxy)-naphthalene of the formula

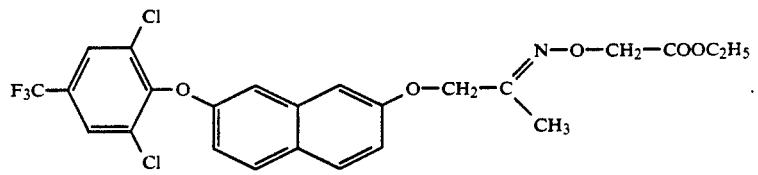

4. A herbicidal composition comprising a herbicidally effective amount of a compound according to claim 1 and a diluent.

5. A method of combating unwanted vegetation which comprises applying to such vegetation or to a locus from which it is desired to exclude such vegetation a herbicidally effective amount of a compound according to claim 1.

6. The method of according to claim 5, wherein such compound is 7-(2,6-dichloro-4-trifluoromethyl-phenoxy)-2-(2-ethoxycarbonylmethoximino-proxoxy)-naphthalene.

7. A compound according to claim 2, in which $R^3$ represents trifluoromethyl.

* * * * *